(12) United States Patent
Weber et al.

(10) Patent No.: US 9,011,516 B2
(45) Date of Patent: Apr. 21, 2015

(54) MEDICAL DEVICES INCLUDING COMPOSITES

(75) Inventors: Jan Weber, Maastricht (NL); Thomas J. Holman, Princeton, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1251 days.

(21) Appl. No.: 11/763,740

(22) Filed: Jun. 15, 2007

(65) Prior Publication Data

US 2008/0161900 A1    Jul. 3, 2008

Related U.S. Application Data

(60) Provisional application No. 60/815,071, filed on Jun. 20, 2006.

(51) Int. Cl.
```
A61F 2/844    (2013.01)
A61F 2/01     (2006.01)
A61F 2/06     (2013.01)
A61F 2/82     (2013.01)
```

(52) U.S. Cl.
CPC . *A61F 2/013* (2013.01); *A61F 2/06* (2013.01); *A61F 2/82* (2013.01); *A61F 2250/003* (2013.01); *A61F 2002/018* (2013.01); *A61F 2230/0006* (2013.01); *A61F 2230/0008* (2013.01); *A61F 2230/005* (2013.01); *A61F 2230/0067* (2013.01); *A61F 2230/0069* (2013.01); *A61F 2230/0078* (2013.01)

(58) Field of Classification Search
CPC .................................................. A61F 2/844
See application file for complete search history.

(56) References Cited

U.S. PATENT DOCUMENTS

| | | | |
|---|---|---|---|
| 5,102,402 A * | 4/1992 | Dror et al. ............. 604/265 |
| 5,195,969 A | 3/1993 | Wang et al. | |
| 5,270,086 A | 12/1993 | Hamlin | |
| 5,320,100 A | 6/1994 | Herweck et al. | |
| 5,674,242 A | 10/1997 | Phan et al. | |
| 6,171,327 B1 | 1/2001 | Daniel et al. | |
| 6,676,987 B2 | 1/2004 | Zhong et al. | |

(Continued)

FOREIGN PATENT DOCUMENTS

| | | |
|---|---|---|
| WO | 2007/086909 | 8/2007 |
| WO | 2007/103356 | 9/2007 |

OTHER PUBLICATIONS

Shi Donglu et al., "Magnetic alignment of carbon nanofibers in polymer composites and anisotropy of mechanical properties," Journal of Applied Physics, American institute of Physics. New York, Mar. 11, 2005.

(Continued)

*Primary Examiner* — Thomas J Sweet
*Assistant Examiner* — Rebecca Preston
(74) *Attorney, Agent, or Firm* — Seager, Tufte & Wickhem, LLC (57) ABSTRACT

Medical devices, such as endoprostheses, and methods of making the devices are described. In some embodiments, a medical device includes an elongated hollow body formed of a polymeric matrix containing one or more regions of a pre-determined weight percent of carbon nanotubes in general alignment in a pre-determined orientation. The medical device can have a compressed state with a first transverse dimension and an expanded state with a second relatively greater transverse dimension.

22 Claims, 8 Drawing Sheets

(56) References Cited

U.S. PATENT DOCUMENTS

| | | | |
|---|---|---|---|
| 6,726,712 B1 | 4/2004 | Raeder-Devens et al. | |
| 7,037,562 B2* | 5/2006 | Jimenez | 428/36.4 |
| 7,238,199 B2* | 7/2007 | Feldman et al. | 623/1.15 |
| 7,462,366 B2 | 12/2008 | Lanphere | |
| 2001/0014821 A1* | 8/2001 | Juman et al. | 623/1.11 |
| 2002/0002399 A1* | 1/2002 | Huxel et al. | 623/1.15 |
| 2002/0038129 A1* | 3/2002 | Peters et al. | 606/167 |
| 2002/0038132 A1* | 3/2002 | Abrams | 606/200 |
| 2002/0103456 A1* | 8/2002 | Roorda | 604/98.01 |
| 2002/0144757 A1 | 10/2002 | Craig et al. | |
| 2003/0018380 A1 | 1/2003 | Craig et al. | |
| 2003/0077200 A1 | 4/2003 | Craig et al. | |
| 2003/0093107 A1 | 5/2003 | Parsonage et al. | |
| 2004/0044397 A1* | 3/2004 | Stinson | 623/1.15 |
| 2004/0117005 A1* | 6/2004 | Nagarada Gadde et al. | 623/1.42 |
| 2004/0143317 A1 | 7/2004 | Stinson | |
| 2004/0171978 A1 | 9/2004 | Shalaby | |
| 2004/0185168 A1* | 9/2004 | Weber et al. | 427/2.1 |
| 2005/0010275 A1 | 1/2005 | Sahatjian | |
| 2005/0070990 A1 | 3/2005 | Stinson | |
| 2005/0216074 A1 | 9/2005 | Sahatjian | |
| 2005/0260355 A1 | 11/2005 | Weber | |
| 2006/0051535 A1* | 3/2006 | Arney et al. | 428/34.1 |
| 2006/0093642 A1* | 5/2006 | Ranade | 424/423 |
| 2006/0153729 A1 | 7/2006 | Stinson | |
| 2006/0173397 A1* | 8/2006 | Tu et al. | 604/8 |
| 2007/0106363 A1* | 5/2007 | Weber | 623/1.11 |
| 2007/0207182 A1 | 9/2007 | Weber | |
| 2007/0207186 A1* | 9/2007 | Scanlon et al. | 424/424 |
| 2010/0185274 A1* | 7/2010 | Moaddeb et al. | 623/1.24 |

OTHER PUBLICATIONS

U.S. Appl. No. 11/368,738, Weber et al., filed on Mar. 6, 2006, 47 pages.

Balaur et al., "Tailoring the wettability of $TiO_2$ nanotube layers," *Electrochem. Commun.*, 7:1066-1070 (2005).

Cao et al., "Super-Compressible Foamlike Carbon Nanotube Films," *Science*, 310:1307-1310 (2005).

Gressel-Michel et al., "From a microwave flash-synthesized $TiO_2$ colloidal suspension to $TiO_2$ thin films," *J. Colloid Interf. Sci.*, 285:674-679 (2005).

Gu et al., "Biomimetic titanium dioxide film with structural color and extremely stable hydrophilicity," *Appl. Phys. Lett.*, 85:5067-5069 (2004).

Karuppuchamy et al., "Cathodic electrodeposition of oxide semiconductor thin films and their application to dye-sensitized solar cells," *Solid State Ionics*, 151:19-27 (2002).

Karuppuchamy et al., "Super-hydrophilic amorphous titanium dioxide thin film deposited by cathodic electrodeposition," *Mater. Chem. Phys.*, 93:251-254 (2005).

"Nanocyl® 3150 series Datasheet—Short Thin Multi-Wall Carbon Nanotubes," Nanocyl S.A., 1 page (Jun. 1, 2005).

Pathan et al., "A chemical route to room-temperature synthesis of nanocrystalline $TiO_2$ thin films," *Appl. Surf Sci.*, 246:72-76 (2005).

Tsyganov et al., "Correlation between blood compatibility and physical surface properties of titanium-based coatings," *Surf Coat. Tech.*, 200:1041-1044 (2005).

Yu et al., "Light-induced super-hydrophilicity and photocatalytic activity of mesoporous $TiO_2$ thin films," *J. Photochem. Photobiol. A: Chemistry*, 148:331-339 (2002).

Ausman et al., *J. Phys. Chem.*, 104(38):8911-15 (2000).

Bahr et al., *J. Am. Chem. Soc.*, 123:6536-43 (2001).

Bronikowski et al., *J. Vac. Sci. Technol.*, 19(4):1800-05 (2001).

Davis et al., *Macromolecules*, 37:154-160 (2004).

Schetsky, L. McDonald, "Shape Memory Alloys", Encyclopedia of Chemical Technology (3rd ed.), John Wiley & Sons, 1982, vol. 20. pp. 726-736.

Streekumar et al., *Chem. Mater.*, 15:175-78 (2003).

* cited by examiner

MEDICAL DEVICES INCLUDING COMPOSITES

CROSS-REFERENCE TO RELATED APPLICATIONS

This application claims priority to U.S. Provisional Application Ser. No. 60/815,071, filed on Jun. 20, 2006. The contents of U.S. application Ser. No. 60/815,071 are incorporated by reference as part of this application.

TECHNICAL FIELD

This invention relates to medical devices, such as endoprostheses (e.g., stents).

BACKGROUND

The body defines various passageways such as arteries, other blood vessels, and other body lumens. These passageways sometimes become occluded or weakened. For example, the passageways can be occluded by a tumor, restricted by a plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, or allowed to expand, so that it can contact the walls of the lumen.

The expansion mechanism may include forcing the endoprosthesis to expand radially. For example, the expansion mechanism can include the catheter with a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force, e.g., absent external application of energy.

SUMMARY

The disclosure relates to medical devices, such as endoprostheses. The invention is based, inter alia, on the discovery that incorporating regions of generally aligned carbon nanotubes into a biodegradable (bioerodable) polymeric matrix allows for generation of medical devices that can both self-expand (with no external application of energy) and biodegrade (bioerode).

In one aspect, the disclosure features medical devices having an elongated hollow body formed of a polymeric matrix containing one or more regions of a pre-determined weight percent of carbon nanotubes in general alignment in a pre-determined orientation.

Embodiments may include one or more of the following features.

The polymeric matrix of the medical device can be biodegradable, e.g., can be a poly(lactic-co-glycolic acid) (PLGA), a polyester (e.g., polylactide and/or poly(E-caprolactone) and/or polytartrate), and/or a polyanhydride (e.g., p(CPP-SA) and/or p(FA-SA)). The polymeric matrix can be biostable, e.g., can be a poly(styrene-b-isobutylene-b-styrene) (SIBS).

The medical device can include biomolecules.

The medical device can have a compressed state having a first transverse dimension and an expanded state having a second relatively greater transverse dimension. The medical device can include one or more self-expanding, local regions of the carbon nanotubes. The medical device can be configured to self-expand, e.g., expand without external application of energy, from the compressed state into the expanded state. The compressed state can include luminal and abluminal grooves aligned approximately perpendicularly to the carbon nanotubes. Biomolecules, e.g., paclitaxel, can further be situated mainly in the abluminal grooves. The device in the compressed state can be configured to fit within the lumen of a delivery catheter and after emission from the delivery catheter to achieve its expanded state, e.g., to self-expand.

The carbon nanotubes are unconnected to each other. The carbon nanotubes can be functionalized. The carbon nanotubes can be single-walled or multi-walled, e.g., double-walled. The carbon nanotubes can be distributed in at least one self-expanding, local region along the length of the medical device. The self-expanding, local region can include at least 10% by weight of carbon nanotubes, e.g., 20% by weight of carbon nanotubes.

At least about 70% by weight of carbon nanotubes may be generally aligned in the pre-determined orientation.

The body of the medical device can be porous. The body of the medical device can be non-porous. The body can be formed into interconnected bands and connectors.

In another aspect, the disclosure features a method for delivery of a medical device, the method including: (i) configuring a medical device having an elongated hollow body formed of a polymeric matrix containing one or more regions of a pre-determined weight percent of carbon nanotubes in general alignment in a pre-determined orientation into a compressed state having a first transverse dimension; (ii) inserting the medical device into a delivery catheter lumen; (iii) emitting the medical device out of the lumen of the delivery catheter; and (iv) permitting the medical device to self-expand, e.g., with no application of external energy, into a state having a second relatively greater transverse dimension.

Embodiments may include one or more of the following features.

The polymeric matrix can be biodegradable, e.g., can be a poly(lactic-co-glycolic acid), a polyester (e.g., polylactide and/or poly(E-caprolactone) and/or polytartrate), and/or a polyanhydride (e.g., p(CPP-SA) and/or p(FA-SA)). In another embodiment, the polymeric matrix can be biostable, e.g., can be poly(styrene-b-isobutylene-b-styrene).

The medical device can include biomolecules.

The medical device in the compressed state can include luminal and abluminal grooves aligned approximately perpendicularly to the carbon nanotubes. Biomolecules, e.g., paclitaxel, can be situated mainly in the abluminal grooves.

The carbon nanotubes are unconnected to each other. The carbon nanotubes can be functionalized. The carbon nanotubes can be single-walled or multi-walled, e.g., double-walled. The carbon nanotubes can be distributed in at least one self-expanding, local region along the length of the medical device. The self-expanding, local region can include at least 10% by weight of carbon nanotubes, e.g., 20% by weight of carbon nanotubes.

At least about 70% by weight of carbon nanotubes may be generally aligned in the pre-determined orientation.

The body of the medical device can be porous. The body of the medical device can be non-porous. The body can be formed into interconnected bands and connectors.

In another aspect, the disclosure features a medical device having a body of: a central region of interconnected bands and connectors forming an elongated tubular structure and defining a central lumen, and proximal and distal regions including a polymeric matrix containing one or more regions of a pre-determined weight percent of carbon nanotubes in general alignment in a pre-determined orientation.

Embodiments may include one or more of the following features.

The polymeric matrix can be biodegradable, e.g., can be a poly(lactic-co-glycolic acid), a polyester (e.g., polylactide and/or poly(E-caprolactone) and/or polytartrate), and/or a polyanhydride (e.g., p(CPP-SA) and/or p(FA-SA)). In another embodiment, the polymeric matrix can be biostable, e.g., can be poly(styrene-b-isobutylene-b-styrene).

The proximal and distal regions can have a radially-compressed state having a first transverse dimension and an expanded state having a second relatively greater transverse dimension. The proximal and distal regions can include one or more self-expanding, local regions of carbon nanotubes. The proximal and distal regions can be configured to self-expand, e.g., expand without external application of energy, from the compressed state into the expanded state. The medical device in the compressed state can include luminal and abluminal grooves aligned approximately perpendicularly to the carbon nanotubes. Biomolecules, e.g., paclitaxel, can further be situated mainly in the abluminal grooves. The device in the compressed state can fit into the lumen of a delivery catheter and after emission from the delivery catheter can achieve its expanded state.

The carbon nanotubes are unconnected to each other. The carbon nanotubes can be functionalized. The carbon nanotubes can be single-walled or multi-walled, e.g., double-walled. The carbon nanotubes can be distributed in at least one self-expanding, local region along the length of the medical device. The self-expanding, local region can include at least 10% by weight of carbon nanotubes, e.g., 20% by weight of carbon nanotubes.

At least about 70% by weight of the carbon nanotubes may be generally aligned in the pre-determined orientation.

Walls of the proximal and distal regions can be porous. Walls of the proximal and distal regions can be non-porous.

In another aspect, the disclosure features a medical device having: (i) a porous membrane with at least one region formed of a polymeric matrix containing a pre-determined weight percent of carbon nanotubes in general alignment in a pre-determined orientation; and (ii) a support shaft carrying the porous membrane.

Embodiments can include one or more of the following features.

The region formed of the polymeric matrix can have a radially-compressed state having a first transverse dimension and an expanded state having a second relatively greater transverse dimension. The medical device can be configured to self expand from the compressed state to the expanded state, e.g., without external application of energy.

The polymeric matrix is biodegradable, e.g., can be a poly(lactic-co-glycolic acid), a polyester (e.g., polylactide and/or poly(E-caprolactone) and/or polytartrate), and/or a polyanhydride (e.g., p(CPP-SA) and/or p(FA-SA)).

At least about 70% by weight of the carbon nanotubes may be generally aligned in the pre-determined orientation.

The compositions and methods described herein provide endoprostheses that can be self-expanding and biodegradable (bioerodable). The described medical devices have the ability to elastically recover large strains and self-expand without external application of energy. The spring force is provided by one or more regions of generally aligned carbon nanotubes that can be placed in numerous types of polymeric matrix. If the polymeric matrix used to generate the medical device is biodegradable, after delivery to the body, the macrostructure of the medical device can be absorbed and removed by the body itself. The matrix of the medical devices can also be filled with biomolecules, and the devices can act as biodegradable drug depots.

The term "biomolecule," as used herein refers to chemical compounds, therapeutic agents, drugs, pharmaceutical compositions and similar substances that can exert biological effects.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification will control. In addition, the materials, methods, and examples are illustrative only and not intended to be limiting. Other features and advantages of the invention will be apparent from the following detailed description, and from the claims.

DETAILED DESCRIPTION

Figure 1A:
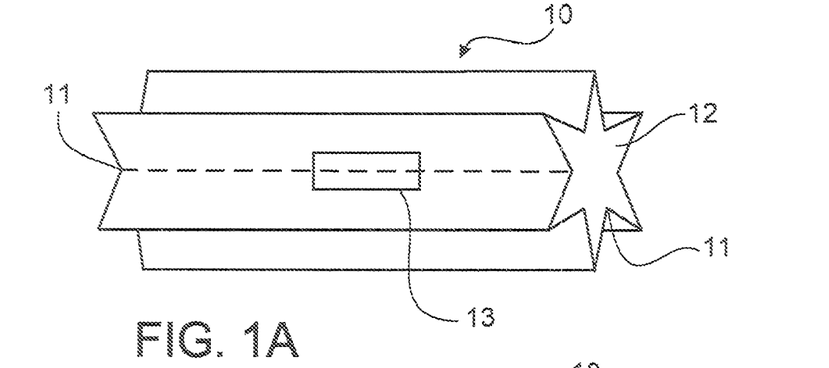
FIG. 1A is a perspective view of a stent in a compressed state.

Referring to FIGS. 1A-1D, a stent 10 has the form of an elongated hollow shaft. Stent 10 has a compressed state as in FIG. 1A with a first transverse dimension and an expanded state as in FIG. 1B with a second, relatively greater, transverse dimension. Stent 10 in the compressed state has abluminal grooves 11 and luminal grooves 12. The shape of stent 10 in the compressed state shown in FIG. 1A is one embodiment only. The shape of stent 10 in the compressed state can differ from the shape shown. One or more regions of the wall 13 forming the body of stent 10 includes polymeric matrix 14 and carbon nanotubes 15 in general alignment in a pre-determined orientation inside the polymeric matrix 14. Preferably, at least 70% of carbon nanotubes 15 are generally aligned within matrix 14. Aligned carbon nanotubes 15 are not connected to each other. The wall 13 forming the body of stent 10 can be porous, i.e., include a plurality of openings (not shown) extending through the wall to allow body fluid and biomolecules to pass through the membrane. The wall 13 can also be non-porous. The wall 13 can be formed into interconnected bands and connectors (i.e., resemble a meshwork) (not shown).

Figure 1B:
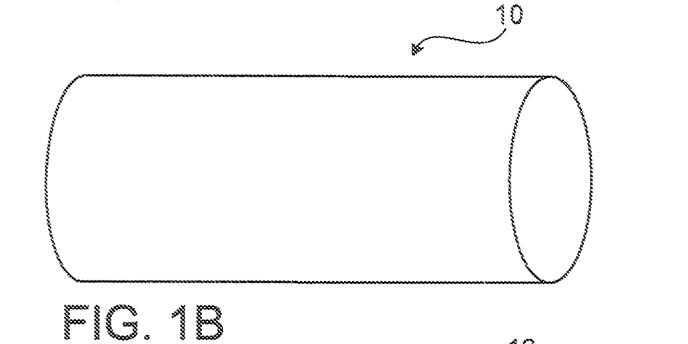
FIG. 1B is a perspective view of a stent in an expanded state.
Figure 1C:
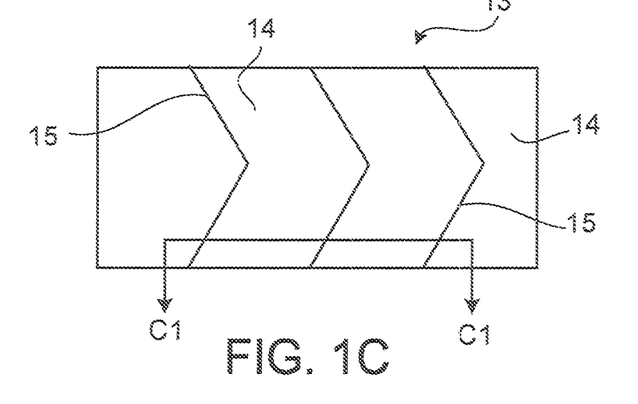
FIG. 1C is a diagram of a section of a wall of the stent.
Figure 1D:
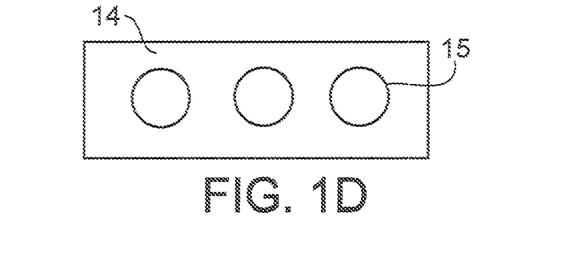
FIG. 1D is a cross-sectional diagram of the stent wall of FIG. 1C, taken along line C1-C1.

The polymeric matrix 14 can be biodegradable. Examples of biodegradable materials that can be used as the polymeric matrix include poly(lactic-co-glycolic acid) (PLGA) and polyurethanes and polyurethane copolymers with the general formula (directly below), where X/Y is, for example, 1 to 20, n is, for example, 2 to 1000, and the total degree of polymerization m is, for example, 2 to 100.

The bioabsorbability of the polymers is enhanced by copolymerization of polyurethane and POSS (polyhedral oligomeric silsesquioxane diol) with suitable monomers. Examples of suitable monomers include caprolactone, ethyleneglycol, ethylene oxide, lactic acid, and glycolic acid. The copolymers from these monomers can hydrolyze and cleave the polymer linkage.

Other examples of biodegradable materials that can be used as polymeric matrix 14 include a general class of polyesters (e.g., polylactide, poly(E-caprolactone), polytartrates) and polyanhydrides (e.g., p(CPP-SA) and p(FA-SA)). The p(CPP-SA) is a copolymer of sebacic acid (SA) and 1,3-bis (p-carboxyphenoxy) propane, while the p(FA-SA) is a copolymer of SA and fumaric acid (FA).

Polymeric matrix 14 can also be biostable and manufactured from such materials as poly(styrene-b-isobutylene-b-styrene) (SIBS). A nylon layer can also be placed over SIBS to improve stability. Examples of polymers that can be used with the disclosed stent are disclosed in U.S. Ser. No. 10/683,314 filed Oct. 10, 2003 and in U.S. Ser. No. 10/958,435 filed Oct. 5, 2004.

Carbon nanotubes are cylindrical carbon molecules that exhibit great strength and unique electrical properties, and are efficient conductors of heat. The oriented carbon nanotubes 15 can be single-walled and multi-walled, e.g., double-walled. Carbon nanotubes 15 can be functionalized. Carbon nanotubes 15 may be generally aligned within the polymeric matrix 14, e.g., alignment of more than 70% of the carbon nanotubes is preferred, using, for example, an AC electric field, as disclosed in U.S. Ser. No. 11/368,738, filed on Mar. 3, 2006. In one embodiment, stent 10 can include at least 10% by weight of carbon nanotubes 15 in at least one self-expanding, local region along the length of stent 10. In another embodiment, stent 10 can include 20% by weight of carbon nanotubes 15 in at least one self-expanding, local region along the length of stent 10. Referring to FIGS. 1A and 1B, stent 10 with such high loading (at least 10% by weight) of carbon nanotubes 15 can be compressed and expand with a low creep spring effect. At least one study has shown that highly-oriented mats of carbon nanotubes can be compressed to folded springs without the effect of creep, Cao et al., *Science* 310:1307-10 (2005).

Thus, the invention provides, inter alia, polymeric, biodegradable (bioerodable) and self-expanding medical devices, e.g., stent 10. Some currently-used self-expanding stents are made of Nitinol, which is not biodegradable. Shape memory polymers are also available, but these materials require heat to restore them to their original shape. The current invention provides self-expanding medical devices that can be designed to expand without the need for external application of energy. The spring force is delivered by the carbon nanotubes described above that can be aligned in various types of polymers, e.g., biodegradable polymers, as outlined above.

The described stents are MRI-compatible because they do not contain ferromagnetic elements and because the construction does not conduct electricity.

Figure 2A:
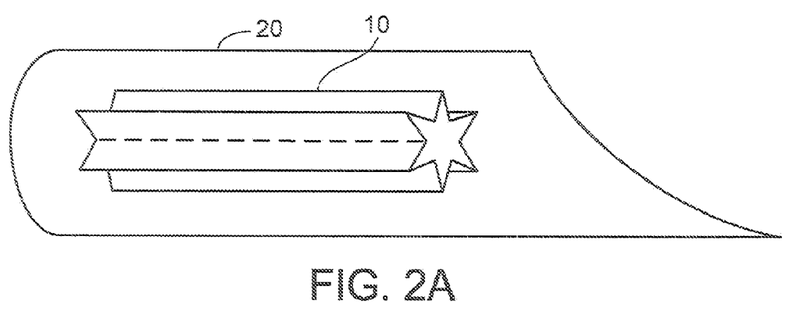
FIG. 2A is a perspective view of a stent in a compressed state inside a delivery catheter.
Figure 2B:
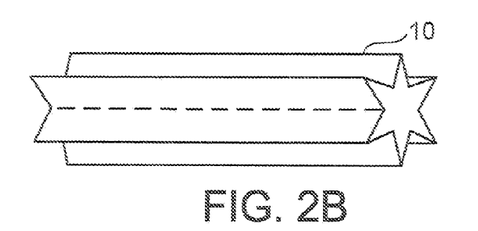
FIG. 2B is a perspective view of the stent in a compressed state emitted from the delivery catheter.
Figure 2C:
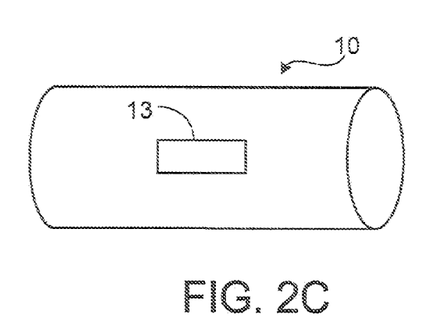
FIG. 2C is a perspective view of the stent in an expanded state.
Figure 2D:
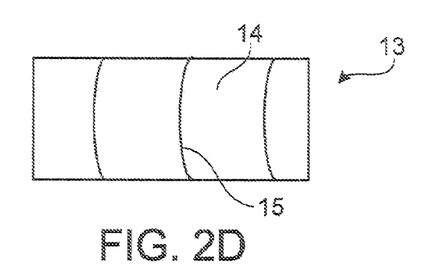
FIG. 2D is a diagram of a section of a wall of the stent.

Referring to FIG. 2A, during use, stent 10 is delivered to a target site via a catheter 20. Stent 10 in its compressed state fits into a lumen of a delivery catheter 20 and is delivered into a vessel. Referring to FIG. 2B, stent 10 is ejected from the catheter 20. Referring to FIG. 2C, stent 10 is permitted to self-expand, e.g., expand without external application of energy, against a wall of the vessel, thereby maintaining the patency of the vessel. As the stent 10 expands, its central lumen opens and allows the blood to flow through it. In a particular embodiment, polymeric matrix 14 forming the wall 13 of stent 10 is biodegradable (bioerodable). After delivery to the vessel, the biodegradable polymeric matrix 14 erodes in the body and exposes carbon nanotubes 15. Because the individual nanotubes 15 are not connected to each other, they can be absorbed by the surrounding tissue or removed, especially functionalized nanotubes that are absorbable in water, for example, nanotubes with COOH or $NH_2$ groups. In this embodiment, the macrostructure of stent 10 disappears from the body. In another embodiment, the polymeric matrix 14 of stent 10 can be biostable. In this embodiment, stent 10 can be removed from the body with a catheter system. Stent 10 can be used, for example, to remove non-obstructive lesions of the vessels.

Catheter systems that can be used with stent 10 are described in, for example, Wang U.S. Pat. No. 5,195,969, Hamlin U.S. Pat. No. 5,270,086, and Raeder-Devens U.S. Pat. No. 6,726,712. Stents and stent delivery are also exemplified by the Radius® or Symbiot® systems, available from Boston Scientific Scimed, Inc., Maple Grove, Minn.

Figure 3A:
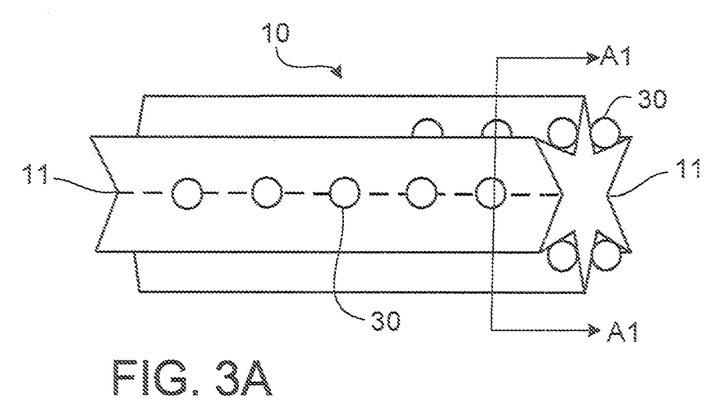
FIG. 3A is a perspective view of a stent in a compressed state with biomolecules situated in abluminal grooves.
Figure 3B:
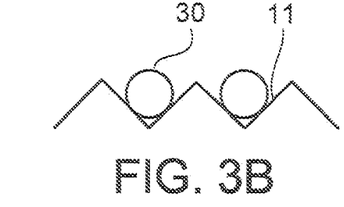
FIG. 3B is a diagram of a cross-section of the stent wall in the compressed state, taken along line A1-A1.
Figure 3C:
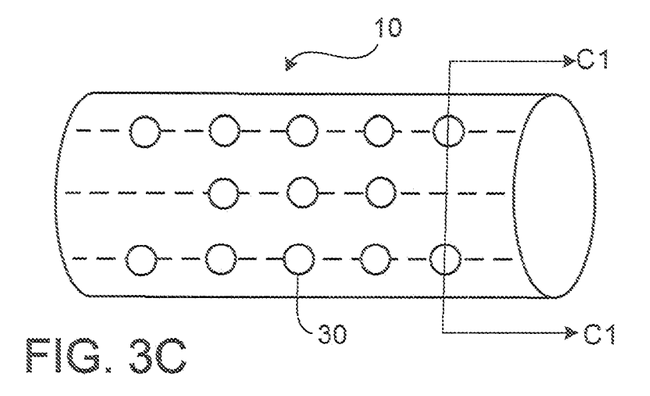
FIG. 3C is a perspective view of the stent in an expanded state with biomolecules.
Figure 3D:
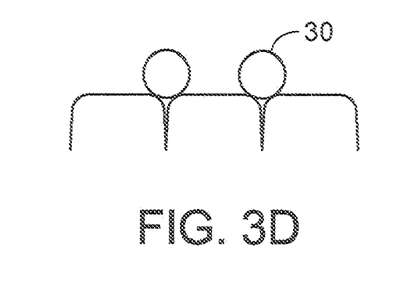
FIG. 3D is a diagram of a cross-section of the stent wall in an expanded state, taken along line C1-C1.
Figure 4A:
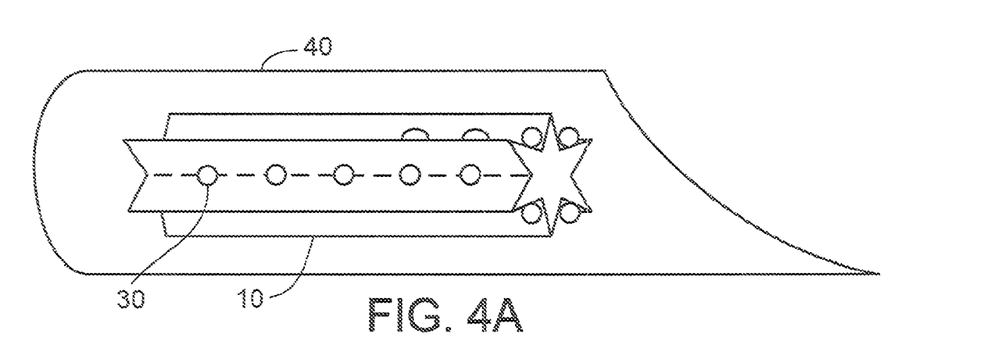
FIG. 4A is a perspective view of a stent in a compressed state with biomolecules inside a delivery catheter.
Figure 4B:
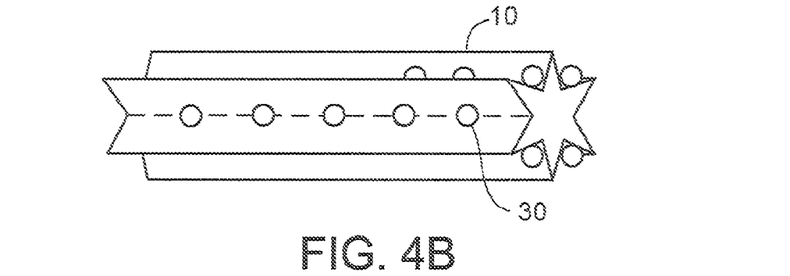
FIG. 4B is a perspective view of the stent in the compressed state with biomolecules after emission from the delivery catheter.
Figure 4C:
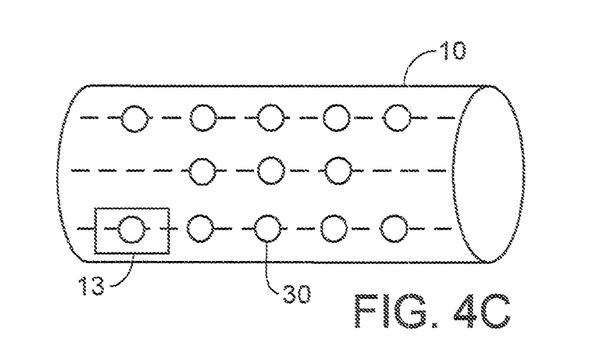
FIG. 4C is a perspective view of the stent with biomolecules in an expanded state.
Figure 4D:
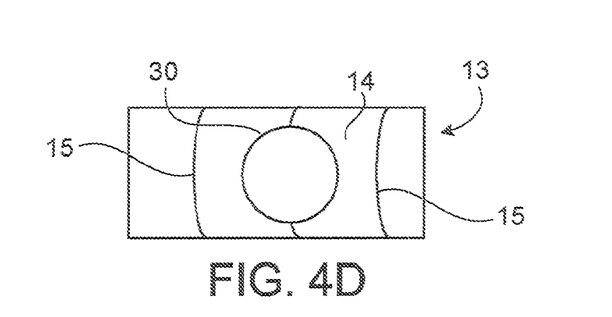
FIG. 4D is a diagram of a section of a wall of the stent.

Further referring to FIGS. 3A and 3B, in a particular embodiment, stent 10 includes biomolecules 30 situated mainly in the abluminal grooves 11. Referring to FIGS. 3C and 3D, expansion of stent 10 exposes biomolecules 30. Biomolecules 30 can include various therapeutic agents, drugs or pharmaceutically active compounds, e.g., paclitaxel and others described in Phan U.S. Pat. No. 5,674,242, Zhong U.S. Pat. No. 6,676,987, and U.S. Ser. No. 10/232,265, filed Aug. 30, 2002. Biomolecules 30 can include, for example, anti-thrombotic agents, antioxidants, anti-inflammatory agents, anesthetic agents, anti-coagulants and antibiotics.

Referring to FIGS. 4A-4D, during use, stent 10 with biomolecules 30 is delivered to a target site via a catheter. Stent 10 with biomolecules 30 in a compressed state fits into a lumen of a delivery catheter 40 and is delivered into a vessel. Stent 10 is ejected from the vessel and permitted to reach an expanded state, e.g., self-expand, e.g., without external application of energy. As stent 10 expands, its lumen opens and the blood flows through it. In a particular embodiment, the polymeric matrix 14 of stent wall 13 is biodegradable. After delivery to the vessel, the matrix 14 degrades, exposing nanosized carbon nanotubes 15 and biomolecules 30. Carbon nanotubes 15 can be absorbed by the surrounding tissue or removed, especially functionalized nanotubes that are absorbable in water, for example nanotubes with COOH or $NH_2$ groups. Biomolecules 30, likewise, can be absorbed by the surrounding tissue or removed by the body itself. In another embodiment, the polymeric matrix 14 of the stent 10 can be biostable. In this embodiment, the stent 10 can be removed from the site with a catheter system.

Figure 5A:
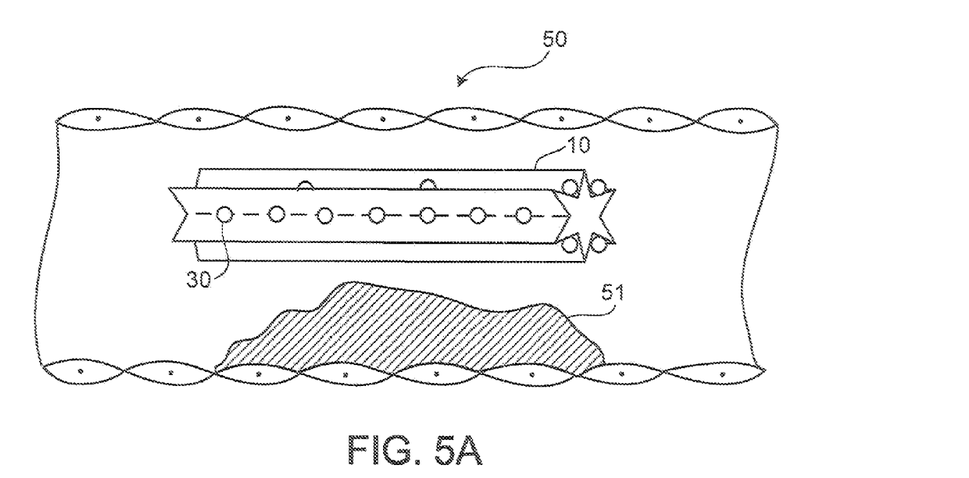
FIG. 5A is a perspective view of a stent in a compressed state inside a blood vessel.
Figure 5B:
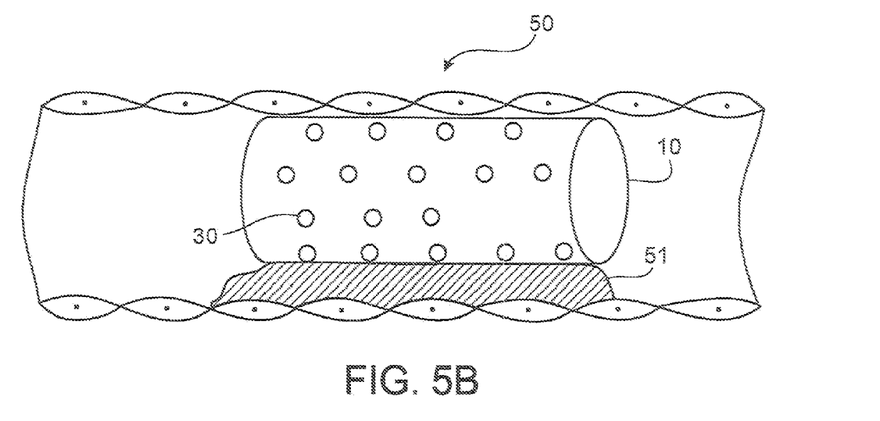
FIG. 5B is a perspective view of the stent in an expanded state inside a blood vessel.

Referring to FIGS. 5A and 5B, stent 10 can be used, for example, to treat blood vessels 50 with vulnerable plaques 51 or non-obstructive lesions 51, e.g., non-obstructive atherosclerotic plaques or non-obstructive thrombotic lesions. Stent 10 can also be used treat or reduce the lesions 51, e.g., with use of biomolecules 30 that target lesions 51. Non-obstructive lesions require access to blood for nutrient supply. Vulnerable plaques (e.g., atheromatous plaques) can rupture and release tissue debris into the blood stream. Thus, shielding lesions or plaques 51 from the blood is advantageous. Such shielding can be accomplished in an embodiment where the wall of stent 10 is non-porous, i.e., does not allow body fluids and/or biomolecules to pass through its wall. Both non-obstructive lesions 51, e.g., lesions that block less than 40% of a blood vessel, and vulnerable plaques 51, can be prone to fissure and disruption. Non-porous stent 10 can resist potential leakage of tissue debris out of ruptured lesions or plaques. Currently-used covered stents are able to avoid some leakage, but in the long term can interfere with the stiffness of the blood vessels. Biodegradable stent 10 is advantageous because it does not remain permanently in the vessel, but rather, as described supra, can degrade and be removed by the body. Current expandable stents, e.g., Nitinol stents, exert a large amount of contact pressure upon expansion. Such high pressure can further disrupt lesion 51 and increase an already-ongoing inflammation of the blood vessel. In addition, Nitinol self-expanding stents prevent MRI screening that can be useful to follow the changes in the lesions. Thus, risk factors associated with the use of currently-available expandable stents limit their use in treating non-obstructive lesions or vulnerable plaques. Referring to FIG. 5A, stent 10 is delivered in a compressed state to a vessel 50 with a non-obstructive lesion or vulnerable plaque 51. Referring to FIG. 5B, stent 10 expands, e.g., self-expands, and contacts the walls of the vessel 50 and the non-obstructive lesion or vulnerable plaque 51. The expansion of stent 10 exerts less contact pressure on the walls of the vessel 50 than currently expandable stents, e.g., Nitinol stents. Stent 10 opens vessel 50, and biomolecules 30 delivered by stent 10 target lesion 51. In one embodiment, stent 10 can be removed after delivering biomolecules 30. In another embodiment, stent 10, consisting of carbon nanotubes and biodegradable polymer can be allowed to degrade and be removed by the body itself. Because contact pressure of stent 10 is low, stent 10 can be used earlier in treatment of non-obstructive lesions than currently-available expandable stents.

Figure 6:
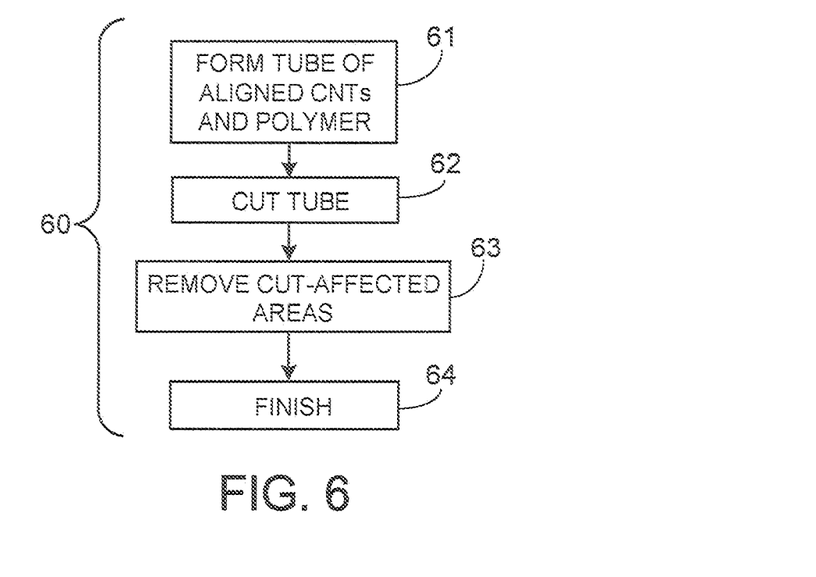
FIG. 6 is a flow chart of an embodiment of a method of making a stent.

Referring to FIG. 6, a method 60 of making stent 10 is described. In one embodiment, stent 10 is manufactured by forming a closed tube shape of polymeric matrix and aligned carbon nanotubes (CNTs), as in step 61. The polymeric matrix 14 is chosen from biodegradable or biostable polymers (as described above). Carbon nanotubes can be mixed into a polymer, e.g., polyamide-12, by common sheer compounding or solvent mixing. Carbon nanotubes can functionalized with such chemical groups as, e.g., COOH, $NH_2$, OH or SH. Biomolecules 30 can also be incorporated into the structure. Alignment of carbon nanotubes 15 within matrix is 14 important for optimizing the mechanical performance. As disclosed in U.S. Ser. No. 11/368,738 filed on Mar. 3, 2006, carbon nanotubes 15 can be aligned using an AC electric field. Preferably, at least 70% by weight of carbon nanotubes are aligned in one or more selected regions in a pre-determined orientation in the method 60. The solid tube is then cut as in step 62 to form stent 10 in a compressed state, the cut-affected areas are removed (step 63) and stent 10 is finished (step 64) by further modification, for example, by addition of biomolecules 30 that are situated mainly in the abluminal grooves 11 of stent 10. In another embodiment, the polymeric matrix 14-carbon nanotubes 15 composite can be directly cast into a stent shape.

Carbon nanotubes 15 are commercially available or can be synthesized. Carbon nanotubes 15 are available, for example, in a mixture from Rice University (Houston, Tex.). Synthesis of carbon nanotubes 15 is described, for example, in Bronikowski et al., *J. Vac. Sci. Technol.*, 19(4):1800-05 (2001); and Davis et al., *Macromolecules*, 37:154-160 (2004). Dispersion of carbon nanotubes 15 in solvents, for example to form a film, is described in Ausman et al., *J. Phys. Chem.*, 104(38): 8911-15 (2000); Streekumar et al., *Chem. Mater.*, 15:175-78 (2003).

In some embodiments, nanotubes 15 can be modified to enhance interactions with the polymeric matrix 14. The dispersion of carbon nanotubes 15 in the polymeric matrix 14 can be achieved by functionalizing the tubes 15, for example by strong acid treatment or by ozone treatment. Nanotubes 15 can be chemically modified with one or more functional groups, e.g., alcohol, carboxylic acid, amide or SH groups, that increase interactions (e.g., compatibility) with the polymeric matrix 14. Functionalization of carbon nanotubes 15 is described, for example, in Bahr et al., *J. Am. Chem. Soc.*, 123:6536-43 (2001), and U.S. Patent Application Publication 2003/0093107. Functionalized carbon nanotubes 15 can also be obtained from Nanocyl S.A. (Belgium; www.nanocyl.com).

Figure 7:
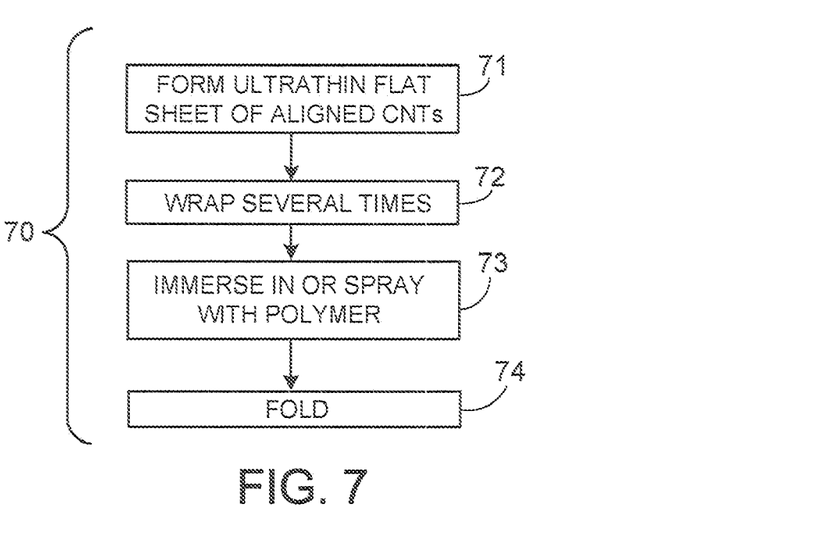
FIG. 7 is a flow chart of an embodiment of a method of making a stent.

Referring to FIG. 7, another method 70 of making stent 10 is described. Stent 10 is manufactured by forming an ultrathin flat sheet of aligned carbon nanotubes 15 (CNTs) (step 71), wrapping it several times in a cigarette roll fashion (step 72) and immersing the structure in a polymeric matrix 14 or spraying the structure with the polymeric matrix 14 (step 73). Stent 10 is then folded into a compressed state (step 74). Stent 10 can also be further modified, for example, by addition of biomolecules 30 that will be situated mainly in the abluminal grooves 11 of the stent.

Stent 10 can be of a desired shape and size (e.g., coronary stents, aortic stents, peripheral vascular stents, gastrointestinal stents, urology stents, and neurology stents). Depending on the application, stent 10 can have a diameter of between, for example, about 1 mm to about 46 mm. In certain embodiments, a coronary stent can have an expanded state diameter of from about 2 mm to about 6 mm. In some embodiments, a peripheral stent can have an expanded state diameter of from about 5 mm to about 24 mm. In certain embodiments, a gastrointestinal and/or urology stent can have an expanded state diameter of from about 6 mm to about 30 mm. In some embodiments, a neurology stent can have an expanded state diameter of from about 1 mm to about 12 mm. An abdominal aortic aneurysm (AAA) stent and a thoracic aortic aneurysm (TAA) stent can have a diameter from about 20 mm to about 46 mm.

Embodiments of stent 10 described above can be used in many medical devices. For example, embodiments can be used as vascular grafts. A graft can be used to replace a damaged or dysfunctional body vessel (e.g., at the site of aneurysm or occlusion), to bypass or divert blood flow around a damaged region, or to create a shunt between an artery and a vein (e.g., for multiple needle access for hemodialysis access). Vascular grafts are described, for example, in Herweck U.S. Pat. No. 5,320,100.

While a number of embodiments have been described above, the invention is not so limited.

Figure 8A:
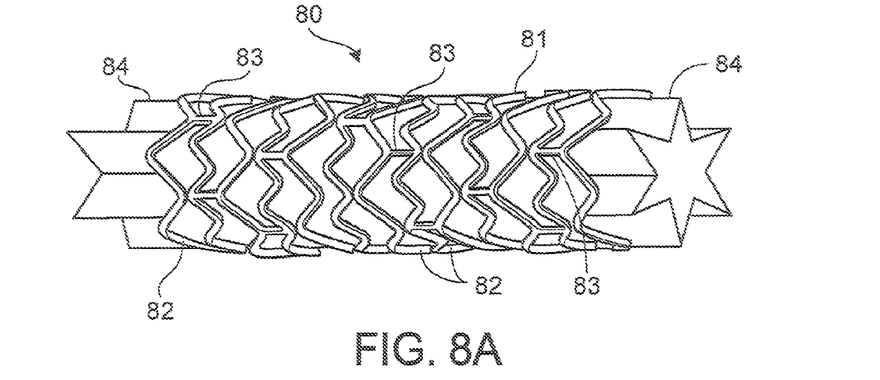
FIG. 8A is a perspective view of a stent with proximal and distal regions in a compressed state.
Figure 8B:
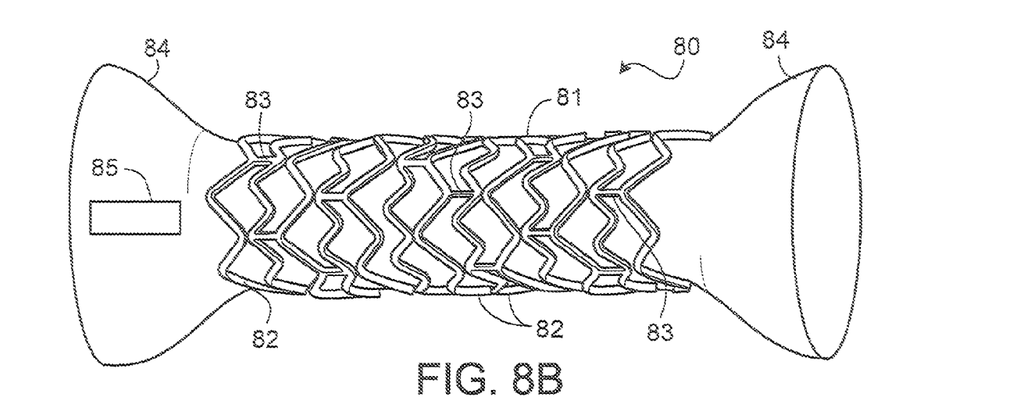
FIG. 8B is a perspective view of the stent with proximal and distal regions in an expanded state.
Figure 8C:
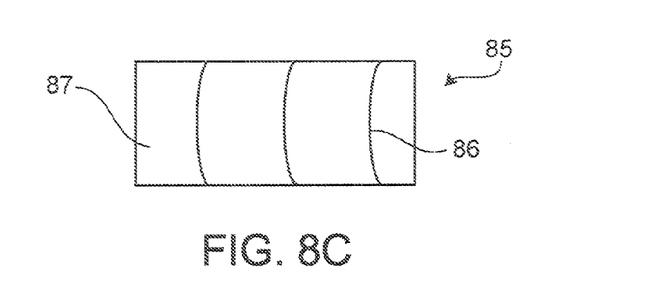
FIG. 8C is a diagram of a section of a wall of the stent.

For example, referring to FIGS. 8A-8C, in another embodiment, stent 80 has a body with central region 81 of interconnected bands 82 and connectors 83 forming an elongated tubular structure and defining a central lumen. Bands 82 and connectors 83 include (e.g., are manufactured from) a metallic matrix. Referring to FIG. 8A, the body of stent 30 also has proximal and distal regions 84 in a radially-compressed state. Referring to FIG. 8B, the proximal and distal regions 84 of stent 80 can self-expand, e.g., expand without external application of energy. Referring to FIG. 8C, the walls 85 of regions 84 can include (e.g., be manufactured from) polymeric matrix 87 containing a pre-determined weight percent of carbon nanotubes 86 aligned in one or more regions in a pre-determined orientation. Preferably, at least 70% by weight of carbon nanotubes are generally aligned. Stent 80 can be used, for example, to prevent restenosis of vessels. Stent 80 can also include biomolecules (not shown) that can target various components of the blood vessels. In one embodiment, walls 85 can be porous, i.e., include a plurality of openings (not shown) extending through the walls to allow body fluid and/or biomolecules to pass through the membrane. In another embodiment, walls 85 can be non-porous.

Examples of materials for metallic matrix of central region 81 include stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. Ser. No. 10/672,891, filed Sep. 26, 2003 and U.S. Ser. No. 11/035,316, filed Jan. 3, 2005. Other materials include elastic biocompatible metal such as a superelastic or pseudoelastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. Ser. No. 10/346,487, filed Jan. 17, 2003.

Figure 9A:
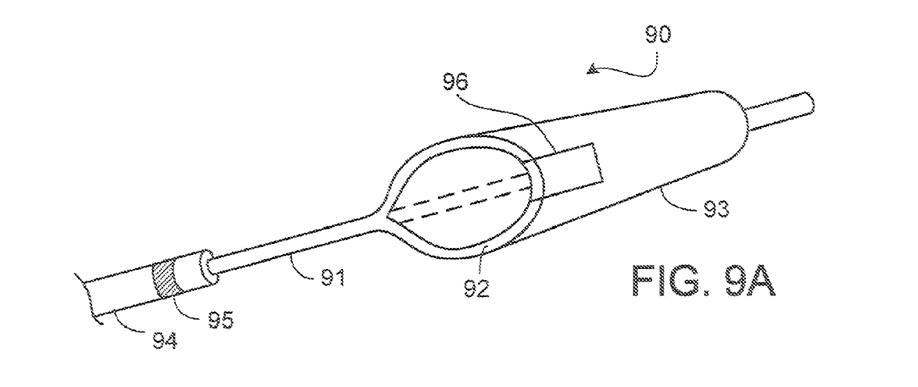
FIG. 9A is a perspective view of an intravascular filter in an expanded state.

Referring to FIG. 9A, in another embodiment, intravascular filter 90 (shown in an expanded state) includes a support shaft 91, a compressible region 92 carried by the support shaft, and membrane 93 supported by the support shaft. Membrane 93 includes a plurality of openings (not shown) extending through the membrane to allow bodily fluid to pass through the membrane. Membrane 93 is connected to shaft 91, for example, by adhesive or by solvent casting methods. During use, filter 90 is delivered to and from a target site through a catheter 94 having a radiopaque band 95. Intravascular filters are further described, for example, in U.S. Ser. No. 10/850,085 filed on May 10, 2004, and Daniel et al., U.S. Pat. No. 6,171,327, and exemplified by the FilterWire EX™ Embolic Protection System, available from Boston Scientific Scimed, Inc., Maple Grove, Minn.

Figures 9B, 9C:
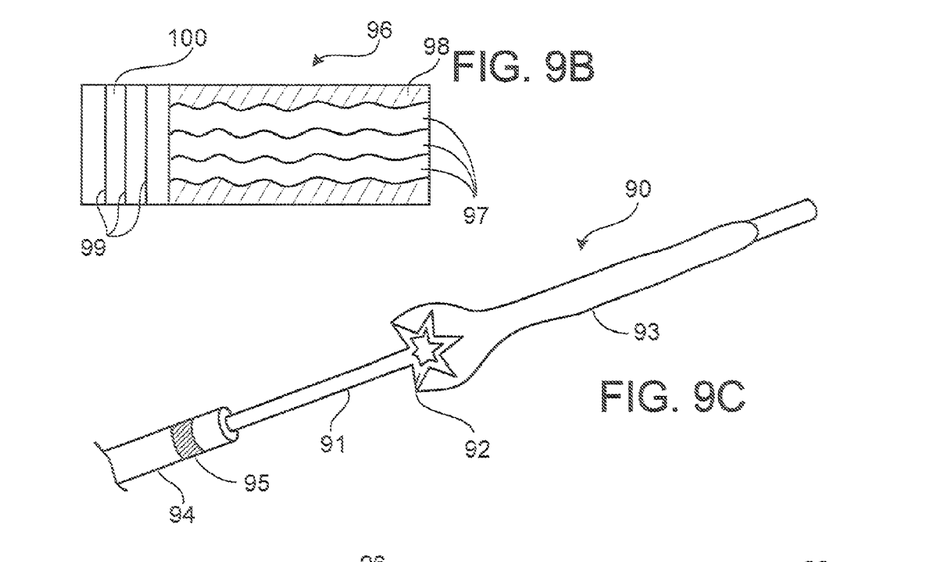
FIG. 9B is a diagram of a section of a wall of an intravascular filter membrane.
FIG. 9C is a perspective view of an intravascular filter in a compressed state.

Currently-available filters include a deformable frame carried by a support shaft and supporting the membrane of the filter, e.g., a Nitinol ring in the FilterWire EX™ Embolic Protection System. The deformable frame is generally stiff and the filter bulky, which makes its passage through narrow lesions difficult. The described embodiment avoids the use of a stiff and fairly large deformable frame, replacing it with at least one radially-compressible region 92. Referring to FIGS. 9A and 9B, wall section 96 of membrane 93 of filter 90 includes relatively porous, nanotube-containing layers 97, sometimes called "bucky paper" or "nanotube paper," between two or more polymer layers 98. Each layer 97 includes a mat of entangled nanotubes. Membrane 93 also includes at least one region 92 of a pre-determined weight percent of generally aligned carbon nanotubes 99 in polymer matrix 100. Preferably, at least 70% by weight of carbon nanotubes are aligned in the pre-determined orientation. Region 92 has high loading of oriented carbon nanotubes 99, e.g., 20% by weight of carbon nanotubes 99. As discussed above, this combination of nanotubes 99 that are not connected to each other in a polymeric matrix 100 allows the region 92 to compress and expand with low creep effect, e.g., self-expand without external application of energy. Thus, region 92 provides flexibility to filter 90. Referring to FIG. 9C, region 92 also allows compression of filter 90 into a small diameter. The smaller the filter diameter, the smaller the vessel through which the filter can pass. During use, filter 90 is delivered through a catheter 94 to and from a target site. Reducing diameter of filter 90 allows reduction of diameter of delivery catheter 94 and decreases risk of trauma when traversing blockage during placement. The target site can be an open blood vessel or a largely-blocked or restenosed blood vessel. Decreasing the diameter of compressed filter 90 widens the range of uses of the filter. Methods of forming membrane 93 of the filter are further described in U.S. Ser. No. 10/850,085, filed on May 10, 2004.

Figure 9D:
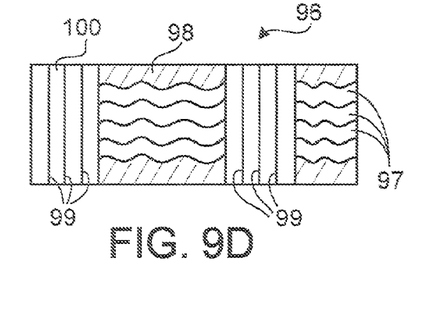
FIG. 9D is a diagram of a section of a wall of an intravascular filter membrane.

Referring to FIG. 9D, in one embodiment, multiple regions with a pre-determined weight percent of generally aligned carbon nanotubes 99 in a polymeric matrix 100 are included throughout membrane 93 of filter 90.

Figure 9E:
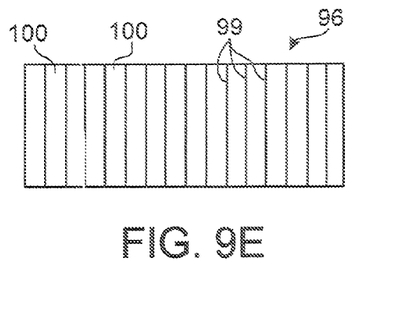
FIG. 9E is a diagram of a section of a wall of an intravascular filter membrane.

Referring to FIG. 9E, in one embodiment, the entire membrane 93 is composed of a pre-determined weight percent of generally aligned carbon nanotubes 99 in a polymeric matrix 100. Thus, in this embodiment, region 92 and membrane 93 are composed of the same material. Membrane 93 includes a plurality of openings (not shown) extending through the membrane to allow bodily fluid to pass through the membrane.

A number of embodiments of the invention have been described. Nevertheless, it will be understood that various modifications may be made without departing from the spirit and scope of the invention. Accordingly, other embodiments are within the scope of the following claims.

What is claimed is:

1. A medical device comprising an elongated hollow body formed of a polymeric matrix containing one or more regions of a pre-determined weight percent of carbon nanotubes, at least 70% of the carbon nanotubes being in general alignment in a pre-determined orientation, wherein the medical device includes at least one biomolecule and has an expanded state and a compressed state, wherein the compressed state defines grooves, the at least one biomolecule being received mainly within the grooves when the medical device is in the compressed state, and the at least one biomolecule being exposed when the medical device is in the expanded state, wherein the polymeric matrix is biodegradable.

2. The medical device of claim 1, further comprising multiple biomolecules.

3. The medical device of claim 1, wherein the medical device in the compressed state has a first transverse dimension and the medical device in the expanded state has a second, relatively greater transverse dimension.

4. The medical device of claim 1, wherein the grooves defined when the medical device in the compressed state include both luminal and abluminal grooves aligned approximately perpendicularly to the carbon nanotubes in general alignment.

5. The medical device of claim 4, wherein the at least one biomolecule is situated mainly in the abluminal grooves.

6. The medical device of claim 1, wherein the carbon nanotubes are unconnected to each other.

7. The medical device of claim 1, wherein the carbon nanotubes are distributed in at least one self-expanding, local region along a length of the medical device.

8. The medical device of claim 7, wherein the self-expanding, local region comprises at least 10% by weight of carbon nanotubes.

9. A medical device having a body of:
(i) a central region of interconnected bands and connectors forming an elongated tubular structure and defining a central lumen; and
(ii) proximal and distal regions each comprising a polymeric matrix containing one or more regions of a pre-determined weight percent of carbon nanotubes, at least 70% of the nanotubes being in general alignment in a pre-determined orientation, wherein the polymeric matrix is biodegradable,
wherein the medical device includes at least one biomolecule and has an expanded state and a compressed state, wherein the compressed state defines grooves, and the at least one biomolecule being received mainly within the grooves when the medical device is in the compressed state, and the at least one biomolecule being exposed when the medical device is in the expanded state.

10. The medical device of claim 9, wherein the proximal and distal regions of the medical device in the compressed state each has a first transverse dimension and in the expanded state each has a second, relatively greater transverse dimension.

11. The medical device of claim 10, wherein the proximal and distal regions each comprises one or more self-expanding, local regions of carbon nanotubes.

12. The medical device of claim 9, wherein the grooves defined when the medical device in the compressed state include both luminal and abluminal grooves aligned approximately perpendicularly to the carbon nanotubes in general alignment.

13. The medical device of claim 12, wherein the at least one biomolecule is situated mainly in the abluminal grooves.

14. The medical device of claim 9, wherein the carbon nanotubes are unconnected to each other.

15. The medical device of claim 9, wherein the carbon nanotubes are distributed in at least one self-expanding, local region along a length of the medical device.

16. The medical device of claim 15, wherein the self-expanding, local region comprises at least 10% by weight of carbon nanotubes.

17. The medical device of claim 1 or 9, wherein the grooves are formed by folding.

18. The medical device of claim 1 or 9, wherein the grooves open upon expansion of the medical device to expose the at least one biomolecule.

19. The medical device of claim 1 or 9, wherein the carbon nanotubes are functionalized to be absorbable upon exposure or to have an enhanced interaction with the polymeric matrix based on the functionalization.

20. The medical device of claim 19, wherein the carbon nanotubes are functionalized by chemical groups comprising COOH, $NH_2$, OH, SH, alcohol, carboxylic acid, or amide.

21. A medical device comprising an elongated hollow body formed of a polymeric matrix containing one or more regions of a pre-determined weight percent of carbon nanotubes, at least 70% of the carbon nanotubes being in general alignment in a pre-determined orientation, wherein the medical device includes at least one biomolecule and has an expanded state and a compressed state, wherein the compressed state defines grooves, the at least one biomolecule being received mainly within the grooves when the medical device is in the compressed state, and the at least one biomolecule being exposed when the medical device is in the expanded state, wherein the medical device comprises one or more self-expanding, local regions of carbon nanotubes.

22. The medical device of claim 21, wherein the polymeric matrix is biodegradable.

\* \* \* \* \*